(12) United States Patent
Meijer Drees et al.

(10) Patent No.: US 9,612,213 B2
(45) Date of Patent: Apr. 4, 2017

(54) AUTOMATIC Z-CORRECTION FOR BASIS WEIGHT SENSORS

(71) Applicants: Reena Meijer Drees, New Westminster (CA); Gertjan Hofman, Vancouver (CA)

(72) Inventors: Reena Meijer Drees, New Westminster (CA); Gertjan Hofman, Vancouver (CA)

(73) Assignee: Honeywell ASCa Inc., Mississauga (CA)

(*) Notice: Subject to any disclaimer, the term of this patent is extended or adjusted under 35 U.S.C. 154(b) by 20 days.

(21) Appl. No.: 14/517,762

(22) Filed: Oct. 17, 2014

(65) Prior Publication Data

US 2015/0323375 A1 Nov. 12, 2015

Related U.S. Application Data

(60) Provisional application No. 61/990,537, filed on May 8, 2014.

(51) Int. Cl.
| | |
|---|---|
| *G01N 23/16* | (2006.01) |
| *G01N 23/09* | (2006.01) |
| *G01G 17/02* | (2006.01) |
| *G01G 9/00* | (2006.01) |

(52) U.S. Cl.
CPC ............ *G01N 23/16* (2013.01); *G01N 23/09* (2013.01); *G01G 9/005* (2013.01); *G01G 17/02* (2013.01); *G01N 2223/04* (2013.01); *G01N 2223/102* (2013.01); *G01N 2223/6425* (2013.01)

(58) Field of Classification Search
CPC ........ G01G 9/005; G01G 17/02; G01N 23/09; G01N 23/16; G01N 2223/6425; G01N 2223/04; G01N 2223/102
USPC ............................................. 250/359.1, 252.1
See application file for complete search history.

(56) References Cited

U.S. PATENT DOCUMENTS

| | | | |
|---|---|---|---|
| 4,276,480 | A | 6/1981 | Watson |
| 4,692,616 | A | 9/1987 | Hegland et al. |
| 5,021,666 | A | 6/1991 | Reber |
| 7,460,233 | B2 | 12/2008 | Kuusela |
| 7,528,400 | B2 | 5/2009 | Duck et al. |
| 8,394,449 | B2 | 3/2013 | Meijer Drees et al. |

*Primary Examiner* — David Porta
*Assistant Examiner* — Gisselle Gutierrez
(74) *Attorney, Agent, or Firm* — Charles H. Jew

(57) ABSTRACT

Nuclear-based basis weight sensors are passline-sensitive. Error in measurement is induced when the sheet moves up and down in the gap between the radiation source and detector. A passline-insensitive basis weight sensor includes a triangulation sensor to measure the position of the sheet within the gap. The sensor and gap is characterized in the laboratory for its passline behavior over a range of basis weights. The curves are either parameterized or a lookup table is created for each weight and passline position and the data added to the sensor's processor. The basis weight measured can be automatically corrected to account for deviations from the passline or nominal path through the sensor.

20 Claims, 2 Drawing Sheets

AUTOMATIC Z-CORRECTION FOR BASIS WEIGHT SENSORS

REFERENCE TO RELATED APPLICATIONS

This application claims priority to U.S. Provisional Application 61/990,537 that was filed on May 8, 2014 and which is incorporated herein by reference.

FIELD OF THE INVENTION

The present invention generally relates to basis weight sensors and more particularly to techniques for automatically correcting for measurement errors introduced by changes in the position of the moving web within the measurement gap.

BACKGROUND OF THE INVENTION

In the forming sheets of material, such as plastics, paper or other web-based products, the sheet is generally formed in a continuous process as a moving film or web. In order to most effectively monitor and control the process, one or more properties of the web must be determined while the web is in motion. The properties of interest include web basis weight, which is the weight per unit area of the web.

To measure the desired web property, one or more sheet sensors are employed in fixed or web traversing structures. The moving web can be constrained to move over a fixed reference surface, but more commonly the moving web is unsupported in the measurement region and is subject to deviations from the nominal path through the measurement region. The nominal path through the measurement region is usually referred to as a "pass-line", and deviations from that pass-line such as "flutter" or other lower frequency deviations alter the pass-line of the web through the measurement region.

A desirable method of forming a measurement region across the width of the web is to utilize nuclear radiation in a traveling sensor arrangement that traverses the moving web to measure the desired web property. A radioactive thickness/density gauge is based upon the principle that a mass of material will absorb the products of radioactive emission in a known and repeatable manner. An industrial web-gauging instrument, known as a beta-gauge, typically utilizes a radioactive isotope that decays through beta particle emission. The radioactive isotope is mounted in an enclosed head or source, which projects the radiation through the web to a second head that includes a radiation detector. The amount of radiation sensed by the detector is directly related to the amount of radiation absorbed by the web material being measured.

The relative position of the moving web in the measurement region space or gap between the source and detector heads is called the web pass-line. Due to the nature of beta particle interaction with the web material, specifically due to the angular dispersion of the beta particles as they pass through the web, the amount of radiation sensed by the detector varies with pass-line deviations. Since the fluctuating web pass-line can vary significantly and at a high frequency during a measurement of the moving web, the accuracy of the gauge or sensor in part depends on the ability to compensate for pass-line variations. In particular, basis weight sensors (especially nuclear-based ones) are passline-sensitive. Error in measurement is induced when the sheet moves up and down in the gap.

SUMMARY OF THE INVENTION

The present invention is based in part on the recognition that a basis weight sensor especially a nuclear-based sensor can be rendered passline-insensitive by characterizing the sensor's passline behavior as a function of sheet weight (not composition) and position within the gap in the sensor.

In one aspect, the invention is directed to a method of measuring the basis weight of a moving sheet of material under test with a sensor that includes a basis weight gauge that includes a radiation source and radiation detector with a gap between the source and detector that defines a radiation path towards a sheet substrate and for detecting the amount of first radiation transmitted through the sheet substrate wherein the transmitted radiation that is detected being an initial measurement of the basis weight of the sheet substrate, said method includes the steps of:

establishing a calibration for the material under test over a range of basis weights and positions within the gap;

moving the sheet of material under test through the gap to obtain an initial basis weight measurement;

measuring the position of the sheet of material within the gap; and determining a final basis weight measurement by correcting the initial basis weight measurement with the calibration.

In another aspect, the invention is directed to a sensor device for measuring the basis weight of a sheet of material that includes:

a basis weight gauge that includes a radiation source and radiation detector with as gap therebetween for directing radiation along a path towards a sheet of material and for detecting the amount of radiation transmitted through the sheet and generating a first signal that corresponds to the radiation transmitted, wherein the first signal corresponds to an initial basis weight measurement of the sheet;

means for measuring the position of the sheet of material within the gap and deriving a correction factor corresponding to the position of the sheet; and means for adjusting the initial basis weight measurement by applying the correction factor.

DESCRIPTION OF THE INVENTION

Figure 1:
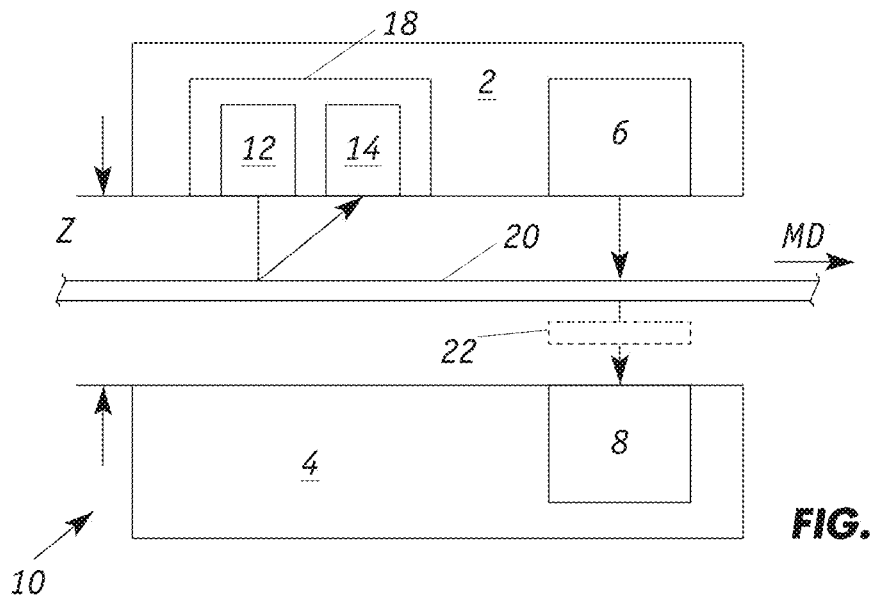
FIGS. 1 and 1A show basis weight sensors with automatic z-correction.

FIG. 1 shows a sensor apparatus 10 for measuring the basis weight of paper and other web product 20. The apparatus includes scanner head 2 that houses a radiation source 6 that emits radiation that is directed along a radiation path toward web or sheet 20, which moves in the machine direction (MD). The radiation can be of the beta type. A radiation detector 8 that is housed in scanner head 4 senses the intensity of radiation that is transmitted through web 20. Sheet 20 is advanced through the gap configured between scanner heads 2 and 4 and the sheet is not supported in the gap and therefore is susceptible to flutter within the gap; the distance z of the gap is preferably fixed. Suitable beta sensors include the 4203 model series of nuclear sensors from Honeywell International, Inc.

The radiation detector senses the amount of radiation absorbed by the web material, which gives an indication of the basis weight (that is, weight per unit area) of the web material. Specifically, the basis weight being inversely proportional to the level of absorption by the material.

With the present invention the passline behavior of the apparatus is determined in the laboratory; particularly for paper products, this behavior is characterized and is a function of sheet mass per unit area (not composition) and position in the gap. The sensor head is outfitted with a single triangulation sensor and in practice the distance to the sheet of paper can be measured to an accuracy of a few microns. With the knowledge of this distance as well as the sheet mass per unit area (from the sensor), a basis weight corrector can be generated based on the characteristic passline curve. With the present invention, it is not necessary to measure the thickness of web 20.

In particular, the apparatus is equipped with a laser triangulation source 12 and detector 14, collectively being referred to as an interrogation laser 18. The source/detector arrangement is referred to generally as a distance determining means. From the measured path length from the source to the detector, values for the distance between each distance determining means and a measurement or interrogation spot on an upper web surface may be determined. The heads 2 and 4 are typically fixed in the position so that the interrogations spots do not move in the machine direction even as the heads are scanned in the cross direction, which is transverse to the machine direction.

Referring to FIG. 1, in the laboratory during the behavior characterization process, standard means can be employed instead of web 20. The standard means has a range of predetermined and stable basis weights that are selectively interposed in the radiation path between scanner heads 2 and 4. The standard means can be polyester (MYLAR from DuPont) disc 22 of a predetermined and stable basis weight which is secured to a frame that is pivoted for rotation on a shaft which is driven through a universal joint by a rotary solenoid unit. For each disc, the standard means is positioned at different vertical positions within the gap. In this fashion, the desired sensor model (and gap) is characterized in the laboratory for its passline behavior over a range of weights.

As shown in FIG. 1, disc 22 is positioned at an initial lower position within the gap adjacent radiation detector 8. Once in position, a conventional gauge measures the distance from the upper surface of disc 22 to the radiation source 6. Finally, as radiation source 6 emits a measurement level of radiation towards disc 22, the radiation detector 8 measures the intensity of the radiation passing through disc 22. All data being is recorded and stored. Thereafter disc 22 is raised to a second position and its distance to the radiation source 6 and the radiation intensity are measured as when disc 22 was at the initial lower position. This behavior characterization process continues with disc 22 being is raised incrementally and measured until a final upper position adjacent radiation source 6 is reached. The initial lower position and the final upper position for disc 22 represent the lowest and highest positions, respectively, in the gap where a web 20 traveling through sensor device 10 might travel. The behavior characterization process next employs a plurality of different sample discs with known basis weights. The laboratory measurements thus establish a library of basis weight measurements using different disc standards that are positioned at different locations within the gap of the sensor device 10. The curves generated by the measurements are either parameterized using standard curve-fitting techniques, or a lookup table is created for each weight and passline position. The inventive method is suited for measuring the basis weight of any web material in which nuclear sensors are applicable. The materials include, for instance, paper, plastic, sandpaper, thin metals and especially non-planar sheets and heavily coated sheet products that exhibit edge curl. In the case of measuring paper, the typical thickness ranges from 20 to 200 microns.

Figure 2:
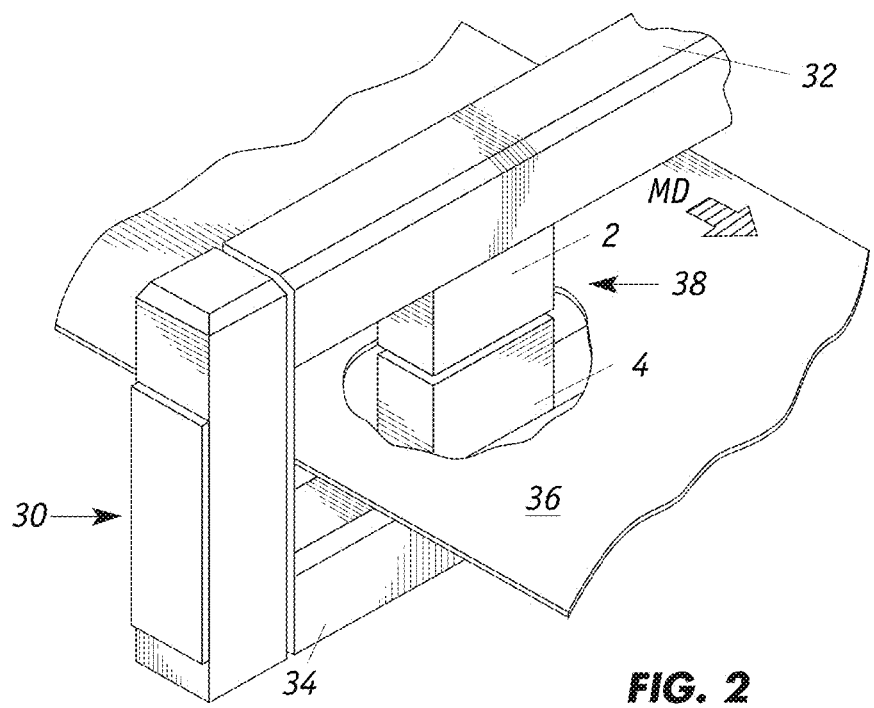
FIG. 2 shows a sheet making system implementing a caliper sensor in a dual head scanner.

FIG. 2 illustrates a scanning sensor system 30 whereby a basis weight sensor is incorporated into a dual head scanner 38 that measures the basis of sheet 36 during continuous production. Scanner 30 is supported by two transverse beams 32, 34 on which are mounted upper and lower scanning heads 2, 4. The operative faces of scanner heads define a measurement gap that accommodates sheet 36.

The movement of the dual scanner heads 2, 4 is synchronized with respect to speed and direction so that the are aligned with each other. The radiation source 6 (FIG. 1) emits radiation onto an illumination (spot) on sheet 36 as the sensor moves repeatedly back and forth in the cross direction (CD) across the width of the moving sheet 36, which moves in the machine direction (MD), so that the basis weight of the entire sheet can be monitored.

Referring to FIG. 1, during operations, basis weight sensor 10 continuously measures the position of sheet 20 within the gap using interrogation laser 18 while radiation source 6 directs a beam of radiation the sheet and radiation detector 8 measures the intensity of the radiation transmitted through the sheet. The intensity of the radiation front the source 6 should be the same as that used during the laboratory behavior characterization phase. By knowing the sheet's position and radiation intensity, the library generated during the above-described characterization phase can be employed to automatically generate the corrected basis weight.

Figure 1A:
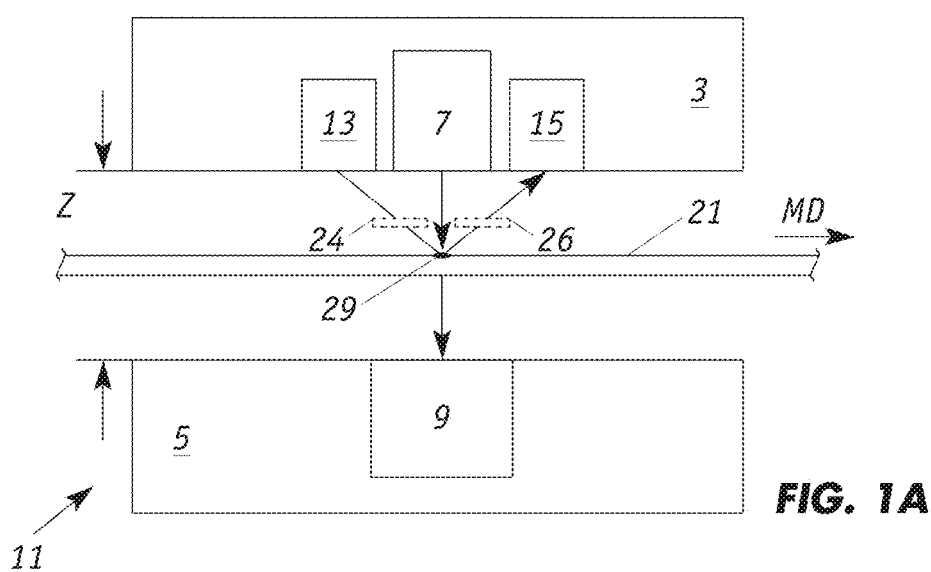

As shown in FIG. 1, the interrogation spot for interrogation laser 18 is upstream of the spot on the sheet where radiation from source 6 passes through the sheet. In the case where sheet 20 remains substantially planar as it passes through gap in sensor 10, the position of sheet 20 as it passes under radiation source 6 is actually measured by the interrogation laser 18. However, in the event sheet 20 does not remain planar, an optical translation technique such as that described in U.S. Pat. No. 7,528,400 to Duck et al., which is incorporated herein, can be employed to move the interrogation spot of the interrogation laser 18 to coincide with basis weight spot where radiation from radiation source 6 is incident on sheet 20. In this fashion, interrogation spot and basis weight spot coincide and both z distance and the transmitted radiation can be measured at the same spot simultaneously. FIG. 1A shows an alternative embodiment of the sensor apparatus 11 that includes (i) scanner head 3 that houses radiation source 7 and laser triangulation source 13 and detector 15 and (ii) scanner head 5 that houses radiation detector 9. A first transparent optical element 24 can be positioned along the path of incident light from laser source 13 so as to refract the light to interrogation spot 29 on the surface of sheet 21. In addition, a second transparent optical element 26 is positioned so that reflected light is refracted into detector 15. In this fashion, the interrogation spot of the triangulation laser coincides with the basis weight spot.

Figure 3:
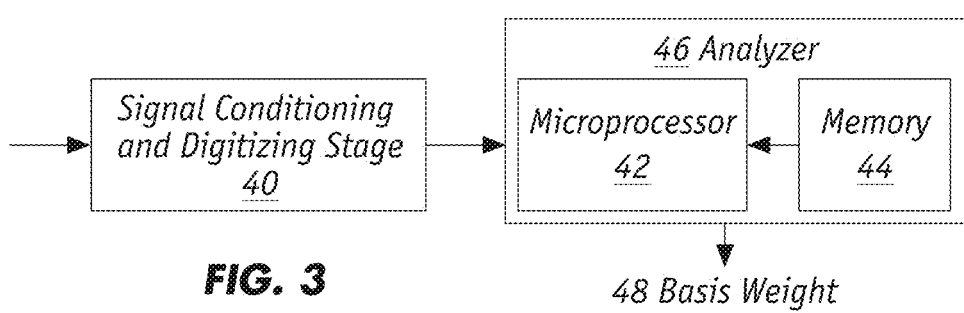
FIG. 3 is a diagram of a system employing process measurements to calculate the final basis weight of the web

FIG. 3 depicts a process for controlling the manufacture of paper or other web product by continuously measuring the basis weight of the web. Digitized signals representing the intensity of the measured radiation transmitted through the web as the position of the web generated by the signal conditioning and digitizing stage 40. A basis weight analyzer 46 includes a microprocessor 42 and memory 44, that contains tables and/or parametric equations, calculates the basis weight signals 48 which can be employed to control actuators upstream and/or downstream of the scanner system 30 (FIG. 2) to regulate production mechanisms in response to the basis weight measurements.

With the present invention, one the sensor apparatus is initially calibrated for a particular material, such as paper, it is not necessary to recalibrate the basis weight sensor each time the web material changes, in thickness or composition such as grade changes. For example, in the production of paper, it is not necessary to recalibrate the sensor when there is a paper grade change as the sensor continues to automatically calculate the basis weight of the sheet product. However, recalibration is necessary when measuring a different type of material such as when the sensor apparatus is switch from measuring paper to plastic or metal. As is apparent, a different calibration library is needed.

The present invention can be implemented by reconfiguring existing nuclear gauges for measuring the basis weight per unit area of the sheet material such as that disclosed in U.S. Pat. No. 4,692,616 to Hegland et al. that is incorporated herein by reference. Once the passline behavior is characterized and the laboratory data stored in a computer, measurements from the gauge can be automatically corrected for variations in the passline to yield accurate basis weight measurements.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A method of measuring the basis weight of a moving sheet of material under test with a sensor that includes a basis weight gauge that includes a radiation source and radiation detector with a gap that is between the source and detector that defines a radiation path towards a sheet substrate and for detecting the amount of first radiation transmitted through the sheet substrate wherein the transmitted radiation that is detected being an initial measurement of the basis weight of the sheet substrate, said method comprising the steps of:

(a) establishing a calibration for the material under test over a range of basis weights and positions within the gap using standards having a range of predetermined and stable basis weights to establish a library of calibration curves or look-up tables wherein the basis weight is the weight per unit area of the sheet of material and wherein step (a) of calibrating the material does not require consideration of the composition of the sheet of material;

(b) moving the sheet of material under test through the gap to obtain an initial basis weight measurement wherein step (b) does not require measuring the thickness of the sheet material;

(c) measuring the z-position of the sheet of material within the gap; and (d) determining a final basis weight measurement by correcting the initial basis weight measurement with the calibration, wherein the basis weight gauge is not recalibrated when the sheet of material changes in grade or thickness.

2. The method of claim 1 wherein step (c) comprises employing a triangulation sensing device.

3. The method of claim 2 wherein the triangulation sensing device includes:

(i) a source of incident radiation that is directed to a surface of the sheet of material and (ii) means for detecting reflected radiation from an interrogation spot on the surface of the sheet of material;

and wherein the method further comprises (e) optically translating the incident radiation such that the interrogation spot is moved to a desired position on the surface of the sheet of material;

(f) optically translating the reflected radiation from the interrogation spot such that the reflected radiation is detected by the means for detecting reflected radiation; and (g) determining the z-position of the interrogation spot within the gap.

4. The method of claim 3 wherein step (b) employs the basis weight gauge to direct radiation from the radiation source to a basis weight spot on the surface of the sheet of material and wherein the interrogation spot and basis weight spot coincide.

5. The method of claim 1 wherein the sheet of material is non-planar.

6. The method of claim 1 wherein the basis weight gauge is a nuclear-based sensor.

7. The method of claim 1 wherein the sheet of material comprises paper, plastic or coated sheet.

8. The method of claim 1 wherein the standards are made of material that is different from that of the material under test.

9. The method of claim 1 wherein the sheet of material moves through the gap in a machine direction and wherein the radiation source is positioned on a first side of the sheet of material and the radiation detector is positioned on a second side of the sheet of material and the method further comprises moving the radiation source and radiation detector in synchronized fashion back and forth along a cross direction to the sheet of material to measure the basis weight of the sheet of material along the cross direction.

10. The method of claim 1 the material under test is paper and the standards are made of polyester.

11. A sensor device for measuring the basis weight of a sheet of material under test that comprises:

a basis weight gauge that includes a radiation source and radiation detector with a gap therebetween for directing radiation along a path towards a sheet of material and for detecting the amount of radiation transmitted through the sheet and generating a first signal that corresponds to the radiation transmitted, wherein the first signal corresponds to an initial basis weight measurement of the sheet, wherein the basis weight is the weight per unit area of the material under test;

means for establishing a calibration for the material under test that comprises standards having a range of predetermined and stable basis weights;

means for measuring the z-position of the sheet of material within the gap and deriving a correction factor corresponding to the position of the sheet; and means for adjusting the initial basis weight measurement by applying the correction factor wherein the means for adjusting the initial basis weight measurement comprises a processor and associated memory containing a library of basis weight calibration curves or look-up tables and the processor is not configured to measure the thickness of the sheet of material.

12. The sensor of claim 11 wherein the means for measuring the position of the sheet of material comprises a triangulation sensing device.

13. The sensor of claim 11 wherein the triangulation sensing device includes:
   (i) a source of incident radiation that is directed to a surface of the sheet of material;
   (ii) means for detecting reflected radiation from an interrogation spot on the surface of the sheet of material;
   (iii) lens that translates the incident radiation such that the interrogation spot is moved to a desired position on the surface of the sheet of material; and
   (iv) lens that translates the reflected radiation from the interrogation spot such that the reflected radiation is detected by the means for detecting reflected radiation.

14. The sensor of claim 13 wherein the basis weight gauge directs radiation from the radiation source to a basis weight spot on the surface of the sheet of material and wherein the interrogation spot and basis weight spot coincide.

15. The sensor of claim 11 wherein the sheet of material is non-planar.

16. The sensor of claim 11 wherein the basis weight gauge is a nuclear-based sensor.

17. The sensor of claim 11 wherein the sheet of material comprises paper, plastic or coated sheet.

18. The sensor of claim 11 wherein the basis weight gauge is not recalibrated when the sheet of material changes in grade or thickness.

19. The sensor of claim 11 wherein the sheet of material moves through the gap in a machine direction and wherein the radiation source is positioned on a first side of the sheet of material and the radiation detector is positioned on a second side of the sheet of material and the radiation source and radiation detector moved in synchronized fashion back and forth along a cross direction to the sheet of material to measure the basis weight of the sheet of material along the cross direction.

20. The sensor of claim 11 wherein the standards are made of material that is different from that of the material under test.

* * * * *